United States Patent [19]

Tanaka

[11] 4,447,374

[45] May 8, 1984

[54] PREPARING REPLICA FILM OF SPECIMEN FOR ELECTRON MICROSCOPY

[75] Inventor: Akira Tanaka, Souka, Japan

[73] Assignee: The Tokyo Metropolitan Institute of Medical Science, Tokyo, Japan

[21] Appl. No.: 356,734

[22] Filed: Mar. 10, 1982

Related U.S. Application Data

[62] Division of Ser. No. 100,280, Dec. 5, 1979, Pat. No. 4,334,844.

[51] Int. Cl.³ .............................................. H05H 1/00
[52] U.S. Cl. ..................................... 264/22; 204/165;
250/311; 250/326; 250/441.1; 250/442.1;
264/81; 264/83; 264/220; 264/221; 427/4;
427/39; 427/41
[58] Field of Search ............. 264/22, 81, 83, 220-221,
264/2.5, 28; 427/4, 39, 41; 250/311, 326, 441.1,
442.1; 204/165; 428/15-17

[56] References Cited

U.S. PATENT DOCUMENTS

| | | | |
|---|---|---|---|
| 2,464,738 | 3/1949 | White et al. | 264/81 |
| 2,875,341 | 2/1959 | Nesh | 250/304 |
| 3,068,510 | 12/1962 | Coleman | 264/22 |
| 3,187,444 | 6/1965 | Lehmann et al. | 428/15 |
| 3,235,630 | 2/1966 | Doherty et al. | 264/2.5 |
| 4,012,475 | 3/1977 | Kindel | 264/28 |
| 4,227,080 | 10/1980 | Okura et al. | 250/311 |
| 4,242,188 | 12/1980 | Niinomi et al. | 427/41 |
| 4,244,992 | 1/1981 | von Hagens | 428/17 |
| 4,278,701 | 7/1981 | von Hagens | 427/4 |

OTHER PUBLICATIONS

"Styrene Resin Cracking Method for Observing Biological Materials by Scanning Electron Microscopy", Journal of Electron Microscopy, Tanaka et al., vol. 23, No. 4, pp. 313-315 (1974).

*Primary Examiner*—Jeffery R. Thurlow
*Attorney, Agent, or Firm*—Armstrong, Nikaido, Marmelstein & Kubovcik

[57] ABSTRACT

A uniform thin replica film of a specimen for electron microscopy having a high resolution power such as approximately 1 Å is presented. This uniform thin replica film is directly prepared on the specimen by a plasma polymerization technique by depositing organic monomer vapors on a specimen placed on a negative electrode in a high vacuum atmosphere. The deposition is carried out by applying a discharge voltage of from 0.5 to 3 K.V.D.C. between a pair of positive and negative electrodes for 1 to 15 minutes to effect a glow discharge under the conditions of a current density of the glow discharge of from 0.1 and 2 mA/cm² and a gas pressure of from 1 to $10^{-2}$ Torr in the system.

2 Claims, 15 Drawing Figures

PREPARING REPLICA FILM OF SPECIMEN FOR ELECTRON MICROSCOPY

This is a division of application Ser. No. 100,280, filed Dec. 5, 1979, now U.S. Pat. No. 4,334,844, issued June 15, 1982.

The present invention relates to a novel replica film of a specimen suitable for use in electron microscopy. More specifically, it relates to a replica film of a specimen having a uniform thickness of approximately from 50 to 1000 Å and having a high resolution power or ability. The present invention also relates to a method and apparatus for preparing said novel replica film of a specimen suitable for use in electron microscopy.

It is known that the resolution power of transmission type electron microscopes reaches 1 Å or less and, therefore, an atomic structure of a special specimen can be analyzed. However, general specimens, especially biological materials, cannot fully utilize the high resolution power of the developed transmission type electron microscopes due to the technical limitation of the conventional replica film preparation. For instance, in the case where the surface of a biological specimen is observed, a scanning type electron microscope is generally used. However, the theoretical resolution power of the scanning type electron microscope is limited to at most approximately 70 Å and, since practical resolution power is far less than the theoretical one, satisfactory results of the observation of ultra-micro structure of biological materials cannot be obtained.

On the other hand, in the case where the surface topography of a specimen is observed by using a transmission type electron microscope, the structure or surface topography of the specimen is observed through a replica film made of a metal which is prepared by, for example, a vacuum evaporation method. However, since grains contained in the metal replica film itself affect the resolution power, the resolution power in this case is generally limited to at most approximately 50 Å. Consequently, if the size of the grains contained in the conventional replica film can be decreased or if a replica film having an amorphous structure can be prepared, the resolution power becomes higher by ten times or more than conventional replica films and, consequently, a striking or remarkable development in the electron microscopical study of the biomedical field can be clearly expected.

Figure 1A:
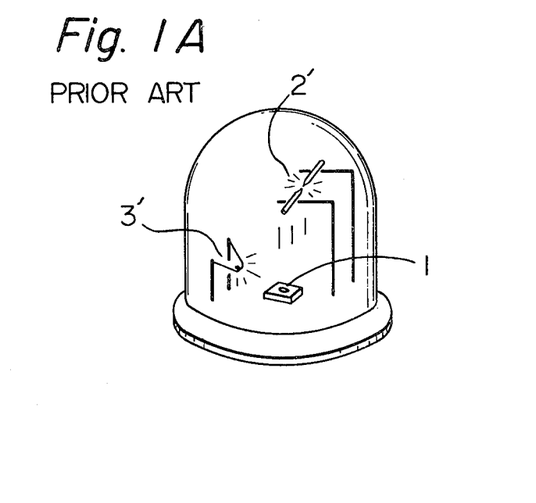
FIG. 1A is a schematic drawing illustrating a fundamental structure of an apparatus for preparing a conventional deposition replica film made of metal.
Figure 2A:
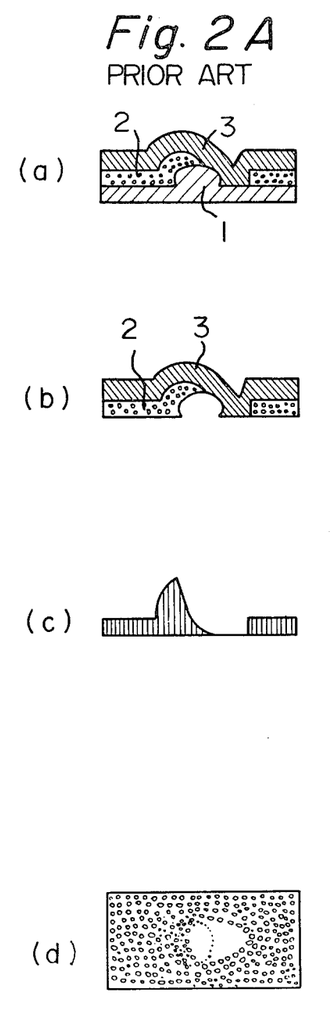
FIG. 2A is a schematic drawing illustrating a general procedure of a conventional single-stage replica method.
Figure 3A:
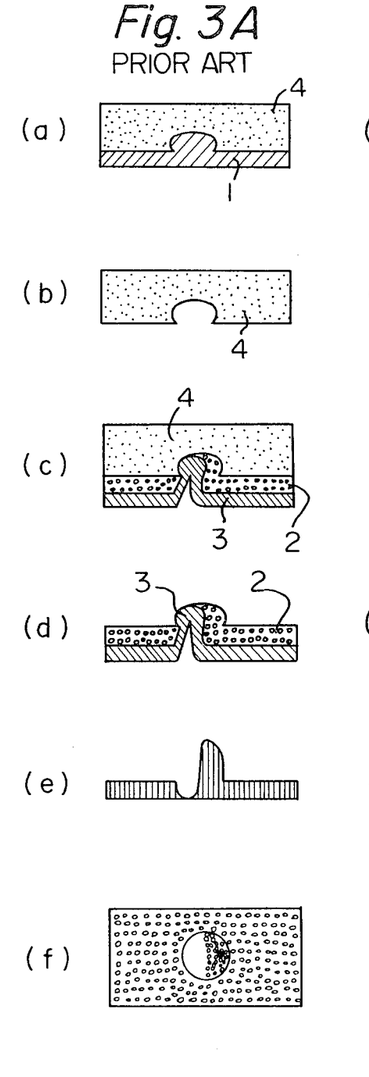
FIG. 3A is a schematic drawing illustrating a general procedure of a conventional two-stage replica method.

Referring to FIGS. 1A, 2A and 3A, the conventional metallic replica technique will now be explained.

Namely, in a vacuum evaporation apparatus as illustrated in FIG. 1A, a heavy metal 3' is evaporated at a vacuum pressure of, for example, approximately $10^{-6}$ Torr and the evaporated metal proceeds at an angle with respect to the horizontal plane and is deposited onto the surface of a specimen 1 which is horizontally placed in the apparatus by means of a so-called "shadow-casting". Then, carbon 2' is evaporated and deposited, as a reinforced film, over the entire surface of the specimen 1. Thus, as illustrated in FIG. 2A-(a), the structure comprising the specimen 1, the deposited metal layer 2 and the deposited carbon layer 3 is obtained. The specimen 1 is then dissolved to form a replica film consisting of two film layers 2 and 3 as illustrated in FIG. 2A-(b). In the case where this replica is observed by transmission type electron microscope, the difference of electron density distribution, as illustrated in FIG. 2A-(c), occurs due to the uneven deposition of the metal and a steric or three dimentional image, illustrated in FIG. 2a-(d), is obtained due to the difference of the density of the transmitted electron beam. This is a fundamental principle of the conventional metallic replica technique.

Further, in the case where the specimen 1 is not dissolved or is not to be dissolved, a so-called two-stage method, as illustrated in FIG. 3A is conducted. That is to say, as illustrated in FIG. 3A-(a), a suitable curable material 4, which cured material is soluble in a solvent, is coated onto the surface of a specimen 1. The cured material layer 4 is then released from the specimen 1. The released surface of the layer 4 corresponds exactly to the surface topography of the specimen 1 to be studied in the electron microscope. On the released surface of the layer 4, the metal layer 2 and the carbon layer 3 as illustrated in FIG. 3A-(c) are successively deposited in manner as described hereinabove. By dissolving the layer 4, a replica film consisting of two layers 2 and 3 as illustrated in FIG. 3a-(d) is obtained. In the case where this replica film is observed by a transmission type electron microscope, the electron density distribution and the steric image as illustrated in FIGS. 3A-(e) and (f), respectively, are obtained.

Figure 5A:
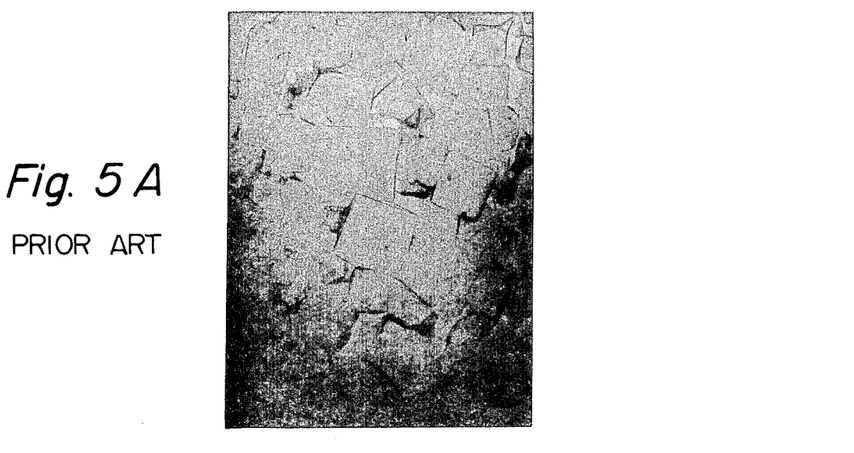
FIG. 5A is an electron photomicrograph ($\times$ 15,000 illustrating replica image of the surface of rock-salt crystals by using a conventional carbon deposition replica film (a single-stage method).
Figure 7A:
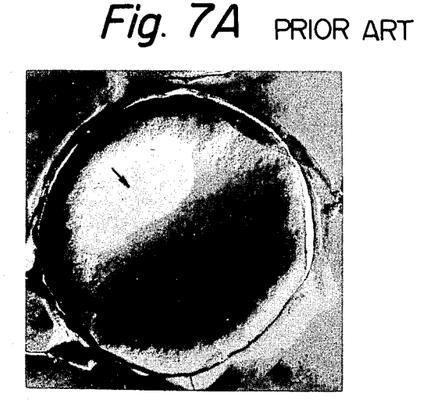
FIG. 7A is an electron photomicrograph ($\times$ 12,000 illustrating a replica image of red blood cells of a mouse by using a single-stage evaporation deposited metallic replica film.

A carbon film or layer contained in the above-mentioned metallic replica film has a structure similar to an amorphous structure from an electron microscopic point of view. However, since the electron density of the carbon layer is very low, a substantial amount of the electron beam transmits through the carbon layer even when a carbon layer having a high thickness is deposited. For this reason, as illustrated in FIG. 5A, a steric image cannot be obtained. Accordingly, in the conventional technique, a replica film, in which concavo-convex contrast (or uneven surface topography of the specimen) is emphasized by means of a so-called "shadow casting" technique, is prepared from a heavy metal having a high electron density. In the case where this replica film is observed by a transmission type electron microscope, a steric image as illustrated in FIG. 7A is obtained. However, in a deposited film derived from a heavy metal, grains having a diameter of approximately 30 Å or more are inevitably formed in such a manner that the minimum distance between the adjacent grains is at least 50 Å. Accordingly, the amount of the deposited metal (i.e. the thickness of the deposited metal layer) should be increased in order to obtain a replica film. However, the causes a problem in that the observed steric image is strongly affected by the difference in the electron density distribution of the transmitted electron beams due to the difference in the deposited amounts of the metal caused by means of the "shadow casting" technique. Therefore, the resolution power of the metallic replica film is naturally limited. Furthermore, as illustrated in a shadow portion, as indicated by an arrow, in FIG. 7A, a portion of the detailed structure of the specimen is often missed in a steric image according to the "shadow casting" method.

The preparation of the metallic replica film according to the above-mentioned vacuum evaporation method was developed 30 years or more ago, and this fundamentally same method is still used at the present time, although some improvements have been effected.

Accordingly, the objects of the present invention are to obviate the aforementioned disadvantages of the conventional replica film for use in electron microscopy and to provide a novel replica film of a specimen having a one-layer amorphous structure and having a high resolution power.

Other objects of the present invention are to provide a novel method and apparatus for preparing said novel replica film of a specimen suitable for use in electron microscopy.

Further objects and advantages of the present invention will be apparent from the description set forth hereinbelow.

In accordance with the present invention, there is provided a replica film of a specimen for electron microscopy comprising a polymer substance derived from plasma polymerization of organic monomer vapors by the glow discharge method, said polymer substance being directly prepared on the surface of the specimen to be tested in the electron microscope, by said plasma polymerization, to form a film having a uniform thickness.

In accordance with the present invention, there is also provided a method for preparing a replica film of a specimen for electron microscopy in an apparatus, which is capable of being maintained at a high vacuum and which contains a pair of positive and negative electrodes parallelly faced with each other with a distance therebetween, comprising the steps of:

(a) placing the specimen on the surface of the negative electrode;

(b) evacuating the atmosphere within the apparatus with a vacuum pump so as to produce a high vacuum of approximately from $10^{-5}$ to $10^{-6}$ Torr within the apparatus;

(c) introducing organic monomer vapors or a mixture thereof with a small amount of an inert gas into the apparatus to produce a gas pressure of approximately from 1 to $10^{-2}$ Torr in the apparatus;

(d) applying a direct discharge voltage of from 0.5 to 3 KV between said two electrodes for 1 to 15 minutes to effect a glow discharge, while the current density of the glow discharge is maintained between 0.1 and 2 mA/cm$^2$ by adjusting the flow rate of the oganic monomer vapors to the apparatus and the flow rate of the evacuation gas from the apparatus, whereby a polymer substance film having a uniform thickness is formed on the surface of the specimen by the diffusion effect of the plasma molecules;

(e) removing the specimen having the polymer substance film thereon from the apparatus after putting the pressure of the atmosphere within the apparatus back to an ordinary pressure; and (f) dissolving the specimen in a solvent which does not dissolve the polymer substance film, but dissolves the specimen, to thereby separate the polymer substance film from the specimen.

In accordance with the present invention, there is further provided an apparatus for preparing a replica film of specimen for electron microscopy comprising:

(a) a pair of electrodes one being an upper positive electrode and the other being a lower negative electrode which parallelly face each other with a distance therebetween and which are placed in a vacuum vessel on a base plate, said both electrodes being electrically and thermically insulated from the vacuum vessel and the base plate;

(b) a direct high-voltage electric source connected to said negative and positive electrodes for effecting a glow discharge between the two electrodes; and (c) means for forming a polymer substance film derived from organic monomer vapors on the surface of a specimen placed on the surface of the negative electrode by plasma polymerization. This apparatus optionally contains (d) additional means for forming the polymer substance film on the surface of the cooled or frozen specimen as a negative electrode block and (e) further means for fracturing the frozen specimen in the vacuum vessel which is used for preparing a replica film of a freeze fractured plane of the specimen.

The present invention will now be illustrated in detail with reference to the accompanying drawings. However, it should be noted that the present invention is not intended to be limited by these drawings.

Figure 1B:
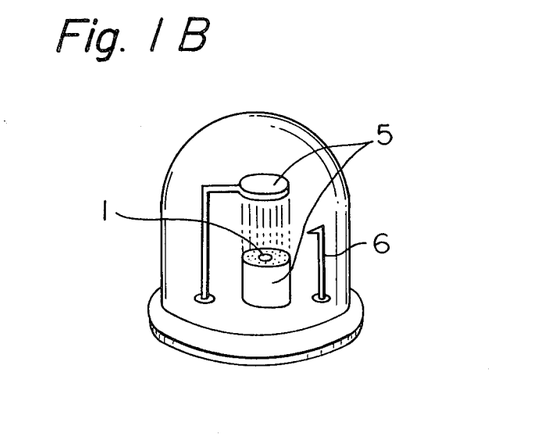
FIG. 1B is a schematic drawing illustrating a fundamental structure of an apparatus for preparing a present replica film made of a polymer substance.
Figure 2B:
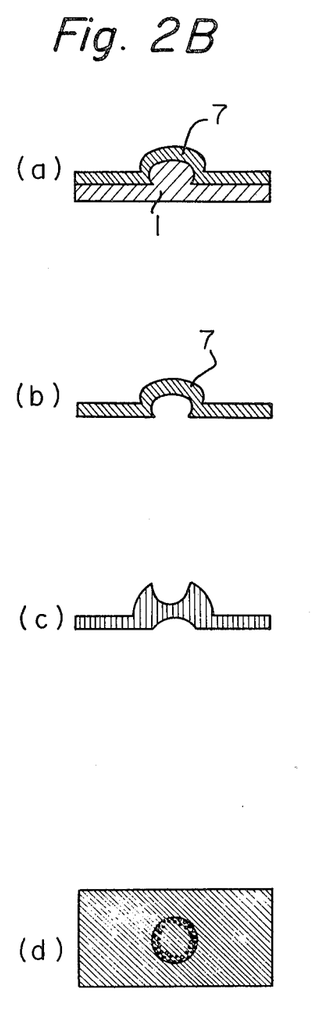
FIG. 2B is a schematic drawing illustrating a general procedure of a single replica method of the present invention.
Figure 3B:
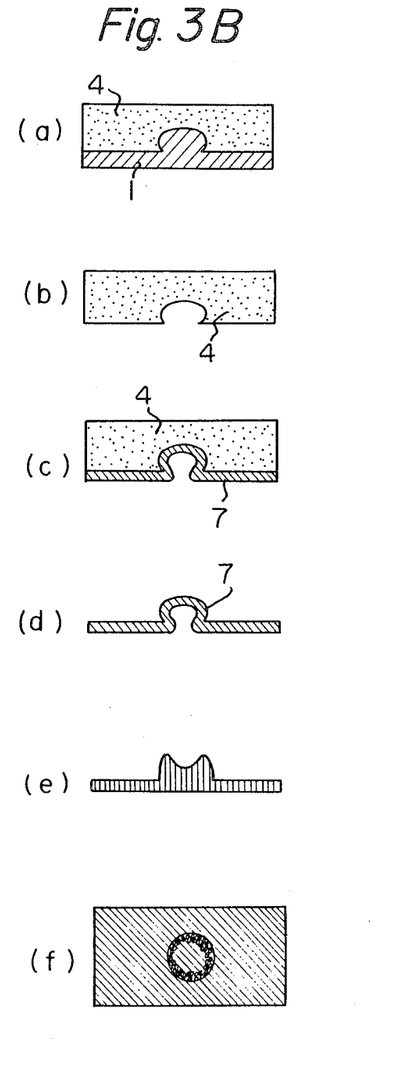
FIG. 3B is a schematic drawing illustrating a general procedure of a two-stage replica method of the present invention.

Referring to FIGS. 1B, 2B and 3B, the present method for preparing a replica film by means of plasma polymerization of organic monomer vapor will now be explained.

As illustrated in FIG. 1B, two spaced apart discharge electrodes 5, the lower of which is a negative electrode and the upper being a positive electrode, are installed in a vacuum vessel and a specimen 1 is placed on the upper surface of the negative electrode. After evacuating the atmosphere from the vessel to produce a high vacuum in the vessel, an organic monomer vapor is introduced into the vessel through a pipe 6 until the gas pressure in the apparatus becomes approximately 0.1 Torr. Then, a direct discharge voltage of from 0.5 to 3 K.V.D.C. is applied between two electrodes to effect a glow discharge. The glow discharge is continued for 1 to 15 minutes under a discharge current density of from 0.1 to 2 mA/cm$^2$, while the surface of the specimen is in a zone between a negative glow phase and a cathod glow phase. Thus, a plasma polymerized film 7 is formed directly on the surface of the specimen as illustrated in FIG. 2B-(a). The specimen 1 is then dissolved in a solvent to form a replica film consisting of the thin plasma polymerized film 7 as illustrated in FIG. 2B-(b). As a solvent, any solvents which can dissolve the specimen can be used. Examples of such solvents are water, aqueous sodium hypochlorite solution, aqueous potassium bichromate, mineral acids such as hydrogen chloride, nitric acid and sulfuric acid, an aqueous solution of sodium hydroxide or potassium hydroxide. The inner surface of this film 7 corresponds exactly to the surface topography of the specimen 1. The electron density distribution of the transmitted electron beams through this replica film is illustrated in FIG. 2B-(c) and the steric image is illustrated in FIG. 2B-(d). The actual steric images observed by an electron microscope are shown in photographs as illustrated in FGS. 5B and 7B.

The two-stage replica method according to the present invention can be carried out, as illustrated in FIG. 3B, in a manner similar to that of FIG. 3A, except that the replica film consisting of a plasma polymerized film 7 is formed, on the inner surface of the cured material 4, by the plasma polymerization described hereinabove. The electron density distribution and the steric image are illustrated in FIGS. 3B-(e) and (f), respectively.

Figure 8:
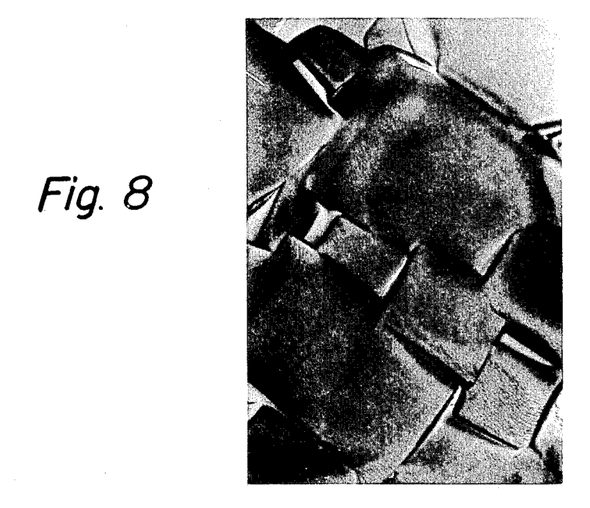
FIG. 8 is an electron photomicrograph ($\times$ 40,000 illustrating a replica image of cooled rock-salt by using a single-stage replica film of the present invention.
Figure 9:
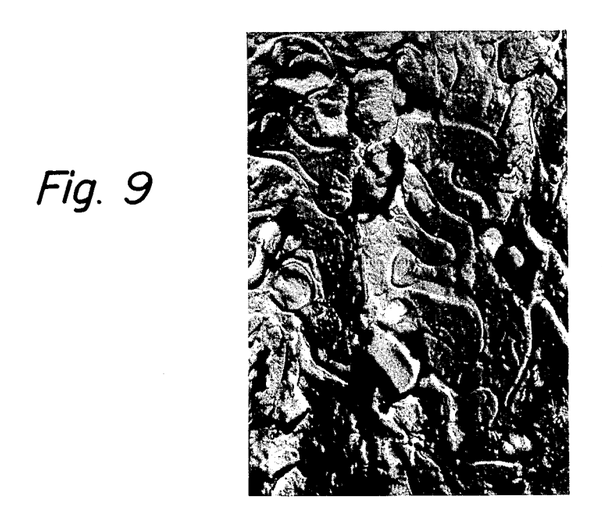
FIG. 9 is an electron photomicrograph ($\times$ 13,000 illustrating a replica image of a freeze fractured plane of a rat kidney by using a single-stage replica film of the present invention.

In the case where a cooled or frozen specimen is observed or where a fractured plane of a frozen specimen such as a piece of a tissue sample is observed, it should be noted that the replica film of the present invention is prepared under different conditions. For instance, if the discharge conditions are the same as in the case of an ordinary temperature sample, a strong replica film may or may not be obtained. In the case where the temperature is less than −50° C., a high discharge energy is required due to the absorption of the heat of the polymerization of the organic monomer vapor. Especially, the glow discharge conditions during the initial period of 10 to 20 seconds are most important to produce a strong replica film on the surface of a specimen. Once a strong ultra-thin film is formed on the surface of the specimen, the deposition of the polymer substance film having a desired thickness can be relatively easily obtained. As mentioned hereinbelow, a replica image of the surface of rock-salt cooled to a temperature of −100° C. is shown in FIG. 8 and a replica image of the frozen fractured surface of a piece of a rat kidney tissue which is frozen at a temperature of −190° C. and then fractured at a temperature of −100° C. is shown in FIG. 9. Thus, a so-called "freeze etching" method can be applied to the present invention.

The plasma polymerization of organic monomer vapors by the glow discharge method is known, and recently, is applied to, for example, the etching of semiconducting materials and the surface treatment of certain special materials such as a small gear wheel. However, in these plasma polymerizations, a most effective high-frequency discharge method is mainly used and studied for efficiently obtaining a thick polymer film having a thickness of tens microns or more. It is not known if a strong thin replica film having a high purity and a uniform thickness formed directly on the surface of a specimen by plasma polymerization of organic monomer vapor in a glow discharge method, and also, if this replica film can be advantageously used for studying the ultra-micro structure of a specimen by a transmission type electron microscope.

The organic monomers used in the present invention can be any compounds which can be plasma polymerized, typical examples of such organic monomers being ethylene, propylene, styrene, benzene, toluene, xylene, chlorobenzene, 1,2,4-trichlorobenzene, ferrocene, ethylbenzene, ethylene chloride, propylene oxide, acrylic compounds such as methyl methacrylate, n-butyl methacrylate, and epoxy compounds such as 1,2-epoxy butane and 1,2-epoxy ethylbenzene. These monomers can be used alone or in any mixture thereof, or a mixture thereof with an inert gas such as argon, helium, neon, nitrogen and the like. The replica films which were used for obtaining the photographs in FIGS. 5B, 6B, 7B, 8 and 9 were prepared by the plasma polymerization of styrene.

Although the optimum glow discharge conditions for obtaining a desired uniform replica film of the present invention depend upon the organic monomer to be used, as well as the kind of specimen and inert gas, the optimum conditions can be easily determined by a person skilled in the art by, for example, previous experimental tests or trial and error methods.

Figure 6A:
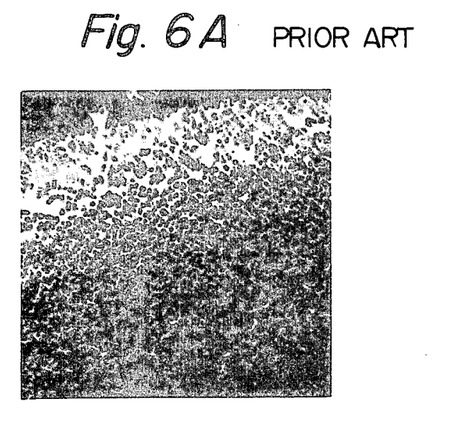
FIG. 6A is an electron photomicrograph ($\times$ 200,000 of a conventional metallic replica film.
Figure 6B:
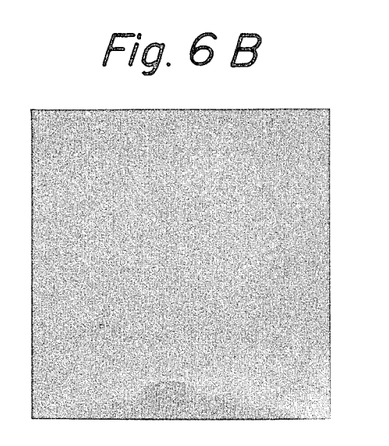
FIG. 6B is an electron photomicrograph ($\times$ 250,000 of the present replica film prepared by plasma polymerization.

The mechanism of forming a uniform and strong thin replica film corresponding exactly to the surface topography of the specimen according to the present invention is not clearly understood. However, it would seem that, without prejudice to the present invention, since plasma or highly ionzed gaseous molecules of an organic monomer have an average energy of approximately 5 to 10 eV, based on the calculation, which is much higher than the average heat energy (i.e. approximately 0.1 eV) of the metal molecules in the conventional vacuum deposition method, these molecules are deposited directly on the surface of a specimen to form a strong and special polymer substance film which is subjected to radical polymerization in situ. In accordance with the glow discharge conditions mentioned hereinabove, the organic monomer is deposited on any specimen of a desired polymer substance film, regardless of the shape, the temperature and the conductivity, of the specimen. The plasma polymerized polymer film of the present invention can even be deposited on any irregular portions of the surface of the specimen in a uniform thickness due to the inherent diffusion effects and dispersive effects of the plasma molecules. The strength and thickness of the plasma polymerized replica film largely depend upon the glow discharge conditions. The replica thin film of the present invention has an amorphous structure, and therefore, grains having a large size, such as approximately 50 Å contained in the conventional metallic replica film, are not contained in the present replica film. This is clear from the photographs in FIGS. 6A and 6B. As illustrated in FIG. 6A, deposited metal grains having a size of approximately 50 Å are observed in the electron photomicrograph of a conventional metallic replica film ( × 200,000 whereas very small points having a distance of approximately 1 to 3 Å can be observed in the electron photomicrograph of the present polymer substance replica film ( × 250,000 ). Accordingly, in the case where the present replica film is used for the observation of the surface topography of specimens, the resolution power is clearly increased by ten or more times compared to the conventional metallic replica film method. Further, since this resolution power of the replica film is comparable to that of an electron microscope (i.e. approximately 1 Å), a remarkable development in the electron microscopical study of, for example, the biomedical field is clearly expected.

A steric image of a specimen is formed, based on the electron beam distribution of the elctron beams which are transmitted through a replica film. However, as mentioned hereinabove, in the case where a metallic replica film is used, a desired steric image cannot be obtained due to the fact that the electron density of carbon film is low. Contrary to this, although the thickness of the plasma polymerized replica film of the present invention is far less than that of the conventional one, a desired steric image can be obtained in the case where the present replica film is used. This is because the electron density of the present replica film is high and the scattering effect of the electron beams due to the present replica film is very large. Especially, the scattering of the electron beams caused by minute irregularity of the surface of the replica film results in a steric image in which contrast is clearly emphasized by the scattering effect of the electron beams. That is to say, in addition to the suitable electron density of the present thin replica film composed of a uniform single layer, when the electron beams penetrate through the flat, inclined and vertical portions in the surface of the present replica film, a difference of the penetration lengths of the electron beams is caused due to the absorption, diffraction and dispersion effects. This difference emphasizes the contrast of the image and generates the density distribution of the transmitted electron beams. As a result, a steric image of the specimen can be clearly observed.

According to the present invention, a steric image of the specimen can be observed by an electron microscope without missing any fine structure of the specimen, whereas the image obtained by using the conventional metallic replica film prepared by the "shadow casting" method is often partially missed as illustrated in FIG. 7A. In addition, there is an outstanding advantage in the present replica film in that the fine structure of the side plane of the replica film can be also observed by tilting the replica film at an appropriate inclination angle $\theta$ during observation in an electron microscope.

The preferred embodiment of the present apparatus for preparing a replica film by plasma polymerization of organic monomer vapors will now be explained.

Figure 4:
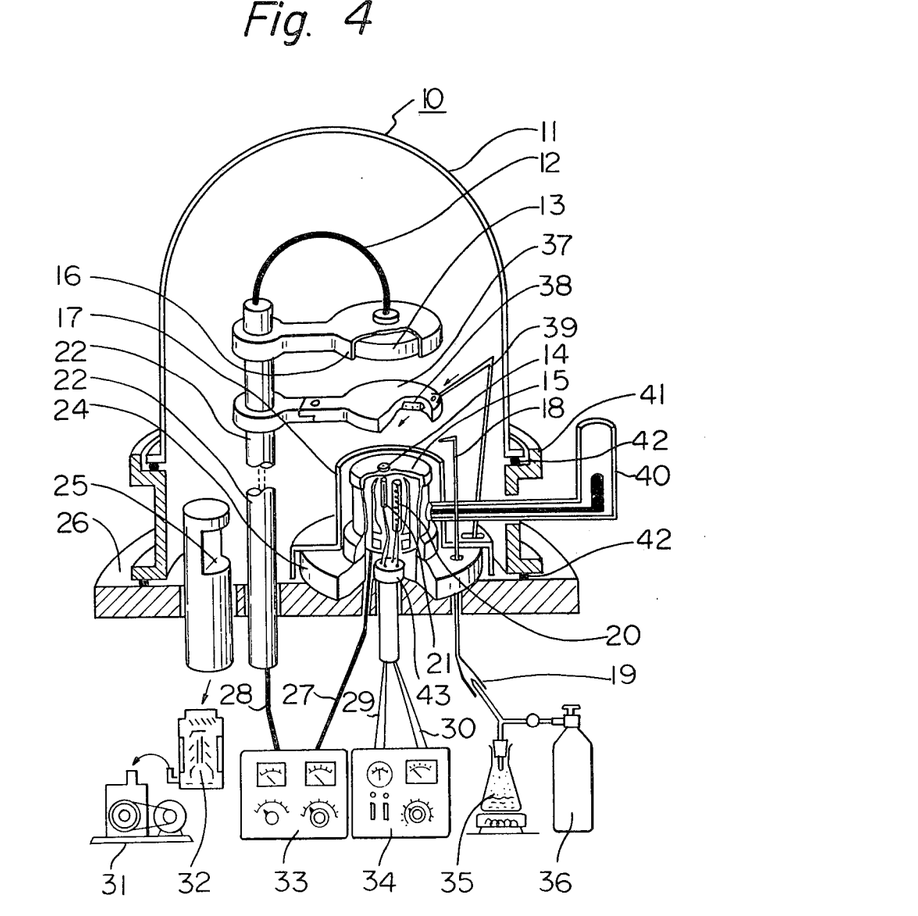
FIG. 4 is a schematic drawing illustrating a structure of a preferred embodiment of an apparatus for preparing the replica film according to the present invention.

As illustrated in FIG. 4, a vacuum vessel 10 is composed of a glass jar 11, a cylindrical adapter 41 made of a metal such as stainless steel and a base plate 26. The connecting portions of these elements are sealed with O-rings 42 for vacuum sealing so as to maintain the inside of the vacuum vessel 10 in a high vacuum state. In the case where a replica film of a specimen having an ordinary temperature is prepared, the glass jar 11 can be directly mounted on the base plate 26 without the use of the cylindrical adapter 41, since a cooling device is not required.

The vacuum vessel 10 is directly connected to an oil diffusion pump 32 and an oil rotary pump 31 through an exhaust or evacuation pipe 25 to produce a high vacuum of, for example, approximately $10^{-6}$ Torr. The oil rotary pump 31 is also set so that the pump 31 can be used alone in order to evacuate the vacuum vessel 10. The typical volume of the vacuum vessel 10 is from 2 to 6 liters, although it can be varied over a wide range. Mounted on the base plate 26 in the vacuum vessel 10 is an insulating plate 24 made of a heat resistant and electrical insulating material such as Duracone, on which negative electrode blocks (14, 15, 20, 21) are mounted.

In the vacuum vessel 10, a pair of electrodes, one being an upper positive electrode 13 and the other being a lower negative electrode 15, both made of, for example, stainless steel, aluminum, duralumin or an electrode plate having a thin platinum layer thereon, is placed. The positive and negative electrodes 13 and 15 parallelly face each other with a variable distance therebetween. Although the distance of the two electrodes is not specifically limited, it generally is variable within the range of from 20 to 100 mm in the case where the volume of the vacuum vessel 10 is from 2 to 6 liters. Typical dimensions of the electrodes are: diameter of the electrodes being from 30 to 100 mm and thickness of the electrodes being from 1 to 30 mm. Generally speaking, it is preferable that the positive electrode 13 is large and thick, whereas the negative electrode 15 is small, from the point of view of heat capacity of the electrode and the damage of the specimen. A specimen support 14 is embeded in the negative electrode 15 in such a manner that the bottom surface of the specimen support 14 is in contact with the uppersurface of the metal cylinder provided with a heating coil 20 and a thermocouple 21, by which the temperature of the specimen support 14 is controlled and measured. The heating coil 20 and the thermocouple 21 are electrically insulated against the negative electrode 15 and connected to a specimen temperature controller 34 through an electric connector 43. A high-voltage wire 27 for the negative electrode 15 connects the negative electrode 15 to a high-voltage electric source controller 33. The negative block is surrounded by a minute discharge prevention cylinder 17, which is grounded to the base plate 26. The inner diameter of the discharge prevention cylinder 17 is generally larger by approximately 6 to 10 mm than the diameter of the negative electrode plate 15.

The positive electrode plate 13 is surrounded with a minute discharge prevention cylinder 16 and supported with a positive electrode support 22.

The positive electrode plate 13 is mounted so as to be horizontally moved around the support 22. The positive electrode 13 is connected to the high-voltage electric source controller 33 through a high-voltage wire 12 for the positive electrode 13, which is wired through the inside of the support 22. The high-voltage source, for example, a high-voltage electric source, can apply either from 0 to 3 KV.D.C. or from 0 to 3 KV.A.C. and can change the polarity thereof. The maximum electric current capacity of the source is, for example 100 mA. A voltage of the glow discharge can be adopted from these ranges, and the discharge holding time can be set by using a timer (not shown).

An organic monomer vapor inlet pipe 18 is inserted into the inside of the vacuum vessel 10 in such a manner that a tip of the inlet pipe 18 from which the organic monomer vapors are discharged is dirrected to the middle portion between the two electrodes 13 and 15. The monomer inlet pipe 18 is connected to a vaporizer 35 of the organic monomer vapors. The organic monomer vapors are generated in the vaporizer 35 at an ordinary temperature or by warming or heating the organic monomer with, for example, an electric heater. These vapors can be optionally diluted with, for example, a very small amount of argon or nitrogen contained in a bomb 36. The organic monomer vapors or a mixture thereof with a diluent gas are introduced into the vacuum vessel 10. The flow rate of the oganic monomer vapors or the mixture thereof with argon or nitrogen is controlled by means of a nozzle 19 (or any appropriate flow control means). The gas pressure within the vacuum vessel 10 can be controlled by adjusting the gas feed rate and the gas evacuation rate. Thus, a constant discharge electric current can be maintained. The discharge electric current and the electric voltage can be measured in the high-voltage electric source controller 33.

In the case where a replica film of a cooled specimen is prepared, the cylindrical adapter 41 is mounted in the vacuum vessel 10 and a liquid nitrogen inlet 40 is attached to the cylindrical adapter 41 in such a manner that the negative blocks (14, 15, 20 and 21) are cooled. The specimen is placed on the cooled specimen support 14. The temperature control can be done by the controller 34.

In the case where a replica film of a freeze fractured tissue is prepared, a device 37 for fracturing a frozen specimen and a cutting lever 39 are additionally installed in the vacuum vessel 10. Further, the specimen support 14 is modified in such a manner that a specimen chip can be inserted into a hole in the specimen support. The cutting means 37 can be made of, for example, stainless steel, and is in a cylindrical form having the same diameter as that of the minute discharge prevention cylinder 17 for a negative electrode. A cutting blade 38 is fixed to the lower portion of the side face of the cutting means 37. The cutting means 37 is horizontally mounted in a level higher by some milimeters than the upper surface of the specimen and is supported by the support 22 in such a manner that the cutting means 37 can be horizontally moved around the support by the external operation out of the vacuum vessel 10. The specimen placed on the specimen support 14 is fractured by strongly forcing the cutting means 37 to a direction shown by an arrow in FIG. 4. After cutting or fracturing the specimen, the cutting means 37 is allowed to be completely removed from the zone between the two electrodes 13 and 15, so that the glow discharge is not obstructed. This cutting can be repeated. In order to freeze the specimen, the tissue specimen is cut into the form of a column having a size of more than approximately 2 mm in diameter and approximately 8 mm in length, and is set in a hole of the specimen support 14 in such a manner that approximately 3 mm in length of the specimen projects out of the upper surface of the specimen support 14. The specimen can be frozen for a short time by using liquid nitrogen and the like together with the cutting means 37 by removing the negative electrode blocks. The negative electrode block can be cooled to a temperature of $-190°$ C. for from 5 to 10 minutes. The cutting means 37 and the negative electrode block are rapidly placed in the vacuum vessel 10 and the atmosphere within the vacuum vessel 10 is evacuated to form a vacuum pressure, for example, approximately $10^{-5}$ Torr. The temperature of the specimen is controlled at an optimum cutting temperature (e.g. $-100°$ C.) by using the heating coil 20. The temperature of the specimen is always monitored by the thermocouple 21. At the optimum cutting temperature (e.g. approximatey $-100°$ C.), the specimen is cut by the cutting means 37 by the action of the cutting lever 39. The frozen fractured plane of the specimen thus obtained is then subjected to vacuum etching for, for example, some seconds to some minutes. Then, Organic monomer vapors previously warmed are introduced into the vacuum vessel 10 to produce a vacuum pressure of, for example, approximately 0.1 Torr in the vacuum vessel 10. A glow discharge is effected by applying, for example, 1.5 to 3 KV.D.C. to the electrodes under a electric current dencity of approximately 0.4 to 1 mA/cm$^2$ for approximately 5 to 15 minutes. The glow discharge condition is higher than that of the ordinary temperature specimen.

According to the present invention, as mentioned hereinabove, the single-stage and two-stage replica film of a general specimen, a well as replica films of a cooled specimen and a freeze fractured specimen, can be effectively and efficiently prepared. These replica films can be advantageously used for electron microscopy in order to study the detailed structure of various specimens.

The present invention now will be further illustrated by, but by no means limited to, the following Examples.

EXAMPLE 1

Preparation of Replica Film of Surface Structure of Ordinary Specimen

By using the apparatus as illustrated in FIG. 4, replica films of various specimens including rock-salt and red blood cells of a mouse were prepared.

Each specimen was placed on a specimen support 14 in a vacuum vessel 10. The atmosphere in the vacuum vessel 10 was then evacuated by an oil rotary pump 31 and an oil diffusion pump 32 through an exhaust pipe 25 to produce a vacuum pressure of from $10^{-5}$ to $10^{-6}$ Torr in the vacuum vessel 10. The distance between a positive electrode 13 and a negative electrode 15 was variable from 30 to 60 mm. The capacity of the high-voltage electric source was from 0 to $\pm 3$ KV.D.C. and from 0 to 3 KV.A.C. The temperature of the specimen which can be monitored in the temperature controller was from $-200°$ C. to $+30°$ C.

Styrene monomer vapors diluted with nitrogen gas were introduced into the vacuum vessel 10 to produce a gas pressure of approximately 1 Torr within the vacuum vessel 10. While the gas pressure within the vacuum vessel 10 was controlled to approximately 0.1 Torr by balancing the styrene vapor feed rate with the gas evacuation rate, a glow discharge was effected for approximately 10 minutes under the electric current density of the glow discharge of approximately 0.4 mA/cm$^2$. In the zone approximately 1 cm above the surface of the negative electrode, a negative violet glow phase was observed. The surface of the specimen was included in this zone. Damages to the specimen and to the negative electrode caused by the shower of the plasma molecules were not observed. The temperature increases in the surface of the specimen was only approximately 15° C. As soon as the glow discharge was commenced, a thin styrene polymer film was deposited over the surface of the specimen. The polymer film having a thickness of approximately 300 Å was obtained in the resultant time of the glow discharge period. The thickness of the polymer film was preferably from approximately 100 to approximately 500 Å for the reason that the damage of the polymer film was minimized during the subsequent specimen dissolving step. The thickness of the polymer film can be easily varied by the holding time of the glow discharge.

After the replica film was prepared by plasma polymerization, the specimen was removed from the vacuum vessel, and then, dissolved in a solvent which does not dissolve the polymer film but dissolves the specimen. Such solvents can be easily determined by those skilled in the art.

Figure 5B:
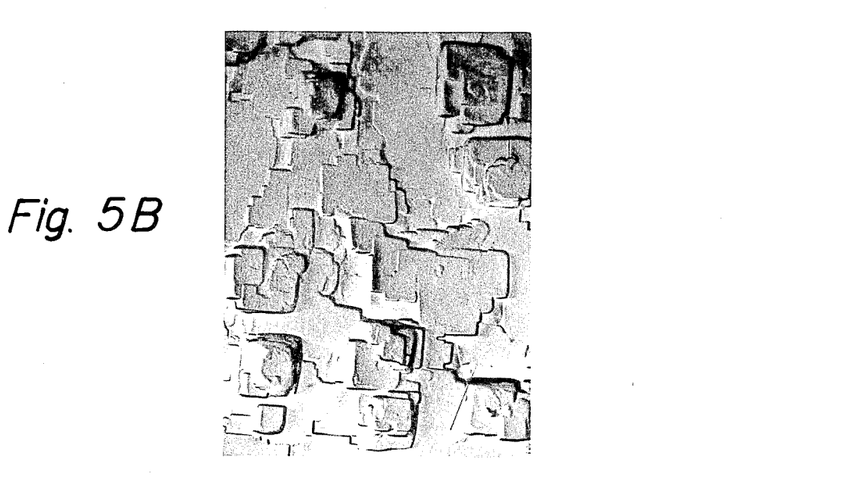
FIG. 5B is an electron photomicrograph ($\times$ 15,000 illustrating replica images of the surface of rock-salt crystals by using the replica film according to the present invention (a single-stage method).

In the case of the rock-salt crystals, the polymer film was directly deposited on the cut surface of the rock-salt having a size of 10 ×10 ×2 mm, which was previously scratched slightly with sand paper. Then, the rock-salt having a deposited polystyrene film thereon was dissolved in water, whereby a replica film made of the polystyrene film by the plasma polymerization of styrene vapor was obtained. The electron photomicrograph (× 15,000) of this replica film is shown in FIG. 5B.

Figure 7B:
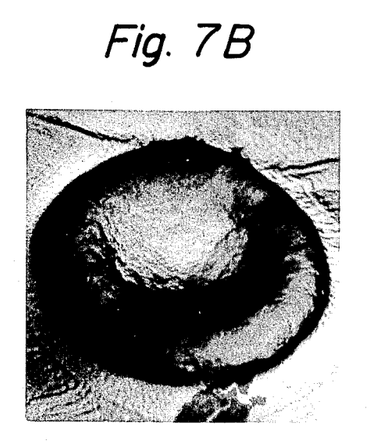
FIG. 7B is an electron photomicrograph ($\times$ 12,000 illustrating a replica image of red blood cells of a mouse by using the present replica film prepared by plasma polymerization.

In the case of the red blood cells of a mouse, the blood collected was fixed for 1 hours in a 2% by weight aqueous glutaraldehyde buffer solution, and then, washed with water. The resultant specimen was subjected to alcohol dehydration, and then, the solvent was substituted by a solvent capable of being rapidly and easily dried, such as acetone, propylene oxide and the like. The solution thus obtained was then rapidly dropped onto, for example, rock-salt or crystallized sugar. The specimen was naturally dried on the rock-salt or crystallized sugar, which was a specimen support. On the specimen, the polystyrene film was directly prepared, as a replica film, by glow discharge under the conditions mentioned hereinabove. The specimen, including the specimen support, was removed from the vacuum vessel and dissolved in water. The rock-salt or crystallized sugar was dissolved in water to form blood cells having the replica film thereon. The specimen was then dissolved in 1 to 5 wt% aqueous sodium hypochlorite for approximately 30 to 60 minutes to thereby form the replica film made of polystyrene. This replica film was observed in a transmission type electron microscope after washing with water. The result is shown in FIG. 7B.

EXAMPLE 2

Preparation of Replica Film of Surface Structure of Cooled Specimen

By using the apparatus as illustrated in FIG. 4, a replica film of cooled rock-salt was prepared. A rock-salt specimen was cut to a size of 10 × 10 × 2 mm and then the cut surface of the rock-salt to be observed was scratched slightly with sand paper.

The set of the negative electrode blocks (14, 15, 20, 21) were taken out of the vacuum vessel 10 and cooled to a temperature of −190° C. with liquid nitrogen. The cooled negative electrode was then set in the vacuum vessel 10 and the rock-salt specimen was placed on the specimen support 14. The vacuum vessel 10 was evacuated and the temperature of the specimen was controlled at −100° C. by using a heating coil. The temperature control was carried out by a controller 34 and the temperature was measured by the thermocouple 21. The polymer film was deposited directly on the cut surface of the rock-salt specimen by plasma polymerization so described on Example 1, except that the following glow discharge condition were used.

Direct Discharge Voltage: 1.5 KV.D.C.
Current Density of Glow Discharge: 0.4 mA/cm$^2$
Glow Discharge Holding time: 10 minutes.

The electron photomicrograph (× 40,000) of the replica film thus obtained is shown in FIG. 8. The specimen was dissolved in water.

EXAMPLE 3

Preparation of Replica Film of Freeze Fractured Plane of Kidney Tissue of Rat

By using the apparatus as illustrated in FIG. 4, a replica film of a freeze fractured plane of a kidney tissue of a rat then prepared. The freeze fractured specimen was prepared as follows. The kidney tissue of a rat was fixed in a 2 wt% aqueous glutaraldehyde solution for one hour, and then, was washed with water. The washed specimen was then soaked in a 25 wt% aqueous gylcerine solution for 3 hours. The specimen thus obtained was cut to a size of approximately 2 × 2 × 8 mm and inserted into a hole mounted in the specimen support. The negative electrode blocks (14, 15, 20, 21) and the cutting means 37 was set and the specimen was frozen to a temperature of −190° C. by using liquid nitrogen. This freezing can be effected outside of the vacuum vessel 10. The vacuum vessel 10 was evacuated to a high vacuum pressure of approximately 10$^{-6}$ Torr. After maintaining this vacuum pressure for more than 30 minutes, the temperature of the specimen was raised to −100° C. under high vacuum pressure and cut by the cutting means 37 at a temperature of −100° C. under the high vacuum pressure. Styrene monomer vapors were immediately introduced into the vacuum vessel 10. After the pressure in the vessel 10 became approximately 0.1 Torr, a glow discharge was effected in a manner as described in Example 1, except that the following conditions were used.

Direct Discharge Voltage: 2 KV.D.C.
Current Dencity of Glow Discharge: 0.5 mA/cm$^2$
Glow Discharge Holding Time: 10 minutes The specimen having polystyrene film thereon was soaked, together with the sample support made of crystallized sugar, in water and, then, in a 1 wt% aqueous sodium hypochlorite, which was previously cooled to a temperature of approximately −20° C. for approximately 1 hour. Thus, the tissue specimen was completely dissolved in the aqueous hypochlorite solution and the replica film was seprated. This replica film was observed on a grid mesh by an electron microscope after washing with water. This electron photomicrograph is shown in FIG. 9.

What is claimed is:

1. A method for preparing a replica of a specimen suitable for use in transmission-type electron microscopy and which is in the form of a film comprising the steps of:
    (a) providing an apparatus comprising a pair of electrodes, one being an upper positive electrode and the other being a lower negative electrode which parallelly face each other with a distance therebetween and which are arranged in a vacuum vessel on a base plate, said pair of electrodes being electrically and thermically insulated from the vacuum vessel and the base plate and being surrounded by minute discharge prevention cylinders;
    (b) placing the specimen on the surface of the negative electrode;
    (c) evacuating the atmosphere within the apparatus with a vacuum pump so as to produce a high vacuum of approximately from $10^{-5}$ to $10^{-6}$ Torr within the apparatus;

(d) introducing organic monomer vapors or a mixture thereof with a small amount of an inert or active gas into the apparatus to produce a gas pressure of approximately from 1 to $10^{-2}$ Torr in the apparatus;

(e) applying a direct discharge voltage of from 0.5 to 3 KV between said two electrodes for 1 to 15 minutes to effect a glow discharge, while the current density of the glow discharge is maintained between 0.1 and 2 $mA/cm^2$ by adjusting the flow rate of the organic monomer vapors to the apparatus and the flow rate of the evacuation gas from the apparatus, whereby a polymer substance film having a uniform thickness is formed on the surface of the specimen by the diffusion effect of plasma molecules;

(f) removing the specimen having the polymer substance film thereon from the apparatus after putting the pressure of the atmosphere within the apparatus back to an ordinary pressure; and (g) dissolving the specimen in a solvent which does not dissolve the polymer substance film, but dissolves the specimen, to thereby separate the polymer substance film from the specimen.

2. A method as claimed in claim 1, wherein said organic monomer is at least one compound selected from the group consisting of ethylene, propylene, benzene, toluene, xylene, styrene, chlorobenzene, 1, 2, 4-trichlorobenzene, ferrocene, ethylbenzene, ethylene chloride, propylene oxide, methyl methacrylate, n-butyl methacrylate, 1,2-epoxy butane and 1,2-epoxy ethylbenzene.

* * * * *